United States Patent
Gjorstrup

(10) Patent No.: US 9,340,483 B2
(45) Date of Patent: May 17, 2016

(54) METHODS OF TREATING AMYOTROPHIC LATERAL SCLEROSIS

(71) Applicant: Anida Pharma Inc., Cambridge, MA (US)

(72) Inventor: Per Gjorstrup, Cambridge, MA (US)

(73) Assignee: ANIDA PHARMA INC., Cambridge, MA (US)

( * ) Notice: Subject to any disclaimer, the term of this patent is extended or adjusted under 35 U.S.C. 154(b) by 0 days.

(21) Appl. No.: 14/379,177

(22) PCT Filed: Feb. 15, 2013

(86) PCT No.: PCT/US2013/026284
§ 371 (c)(1),
(2) Date: Aug. 15, 2014

(87) PCT Pub. No.: WO2013/123290
PCT Pub. Date: Aug. 22, 2013

(65) Prior Publication Data
US 2015/0010549 A1    Jan. 8, 2015

Related U.S. Application Data

(60) Provisional application No. 61/599,096, filed on Feb. 15, 2012.

(51) Int. Cl.
*A61K 31/202* (2006.01)
*C07C 59/42* (2006.01)
*A61K 45/06* (2006.01)

(52) U.S. Cl.
CPC .............. *C07C 59/42* (2013.01); *A61K 31/202* (2013.01); *A61K 45/06* (2013.01)

(58) Field of Classification Search
CPC ...................................... A61K 31/202
USPC .......................... 514/165, 475, 560
See application file for complete search history.

(56) References Cited

U.S. PATENT DOCUMENTS

| 2003/0130350 A1* | 7/2003 | Ramesh et al. ............... 514/564 |
| 2004/0254152 A1* | 12/2004 | Monje et al. ................. 514/165 |
| 2005/0075398 A1* | 4/2005 | Bazan ................. A61K 31/202 514/560 |
| 2009/0156673 A1* | 6/2009 | Serhan et al. ................. 514/549 |
| 2010/0267828 A1 | 10/2010 | Holmeide et al. |
| 2011/0190389 A1* | 8/2011 | Arterburn ............ A23L 1/3008 514/475 |

* cited by examiner

*Primary Examiner* — Kamal Saeed
*Assistant Examiner* — Janet L Coppins
(74) *Attorney, Agent, or Firm* — Mintz, Levin, Cohn, Ferris, Glovsky and Popeo, P.C.

(57) ABSTRACT

The present invention relates to use of DHA analogs and their pharmaceutical compositions for treating ALS, by administering these compounds or pharmaceutical compositions to subjects in need thereof.

20 Claims, 5 Drawing Sheets

METHODS OF TREATING AMYOTROPHIC LATERAL SCLEROSIS

CROSS-REFERENCE TO RELATED APPLICATIONS

This application is a national stage application, filed under 35 U.S.C. §371, of International Application No. PCT/US2013/026284, filed Feb. 15, 2013, which claims priority to and benefit of U.S. Provisional Application No. 61/599,096, filed Feb. 15, 2012, the contents of each of which are incorporated herein by reference in it's their entirety entireties.

BACKGROUND OF THE INVENTION

Amyotrophic lateral sclerosis (ALS) is an incurable fatal motoneuron disease with a lifetime risk of 1:800. It is characterized by progressive weakness, muscle wasting and death ensuing 3-5 years after diagnosis. Currently, the only available treatment option is riluzole that prolongs life by 2-3 months, with questionable functional improvement. Accordingly, new compounds and methods for treating ALS are needed. The present invention addresses these needs.

SUMMARY OF THE INVENTION

The present invention provides, in part, a method for treating amyotrophic lateral sclerosis (ALS). The method includes administering to a subject in need thereof a therapeutically effective amount of a compound of Formula I, II, III or IV:

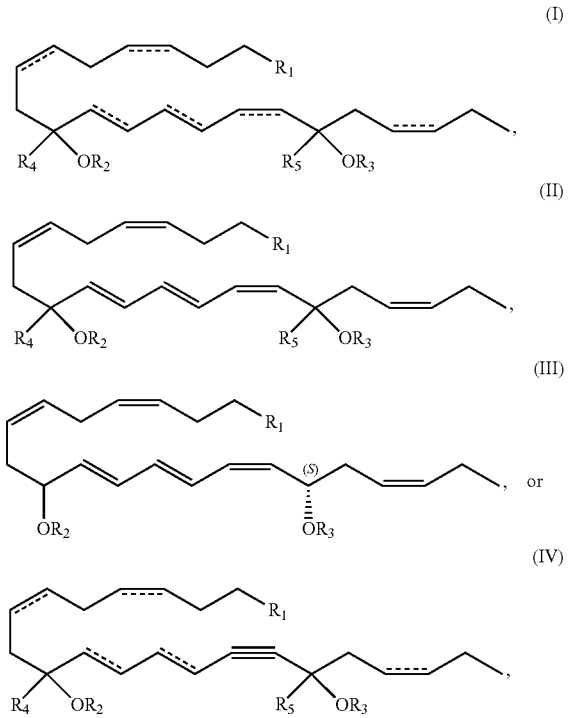

or a pharmaceutically acceptable salt, ester, solvate, hydrate or prodrug thereof. In Formula I, II, III, or IV:
- - - - - represents a cis or trans bond;
$R_1$ is —C(O)O$R_a$, —C(O)N$R_b R_c$, —C(O)H, —C(NH)N$R_b R_c$, —C(S)H, —C(S)O$R_a$, —C(S)N$R_b R_c$, or —CN;
$R_2$ and $R_3$ are each independently H or a protecting group;
$R_4$ and $R_5$ are each independently H, halo, unsubstituted or substituted $C_1$-$C_6$ alkyl, unsubstituted or substituted $C_3$-$C_{10}$ carbocycle, unsubstituted or substituted heterocycle comprising one or two 3-, 4-, 5- or 6-member rings and 1-4 heteroatoms selected from N, O and S;
$R_a$ is a protecting group or -$T_1$-$Q_1$;
$R_b$ and $R_c$ are each independently a protecting group or -$T_1$-$Q_1$, or $R_b$ and $R_c$, together with the nitrogen atom to which they are attached, form an unsubstituted or substituted heterocycle comprising one or two 5- or 6-member rings and 1-4 additional heteroatoms selected from N, O and S;
$T_1$ is a bond or unsubstituted or substituted $C_1$-$C_6$ alkyl linker; and
$Q_1$ is H, hydroxyl, halogen, unsubstituted or substituted $C_1$-$C_6$ alkyl, unsubstituted or substituted $C_1$-$C_6$ alkoxy, unsubstituted or substituted 2-6 membered heteroalkyl, unsubstituted or substituted $C_3$-$C_{10}$ carbocycle, or unsubstituted or substituted heterocycle comprising one or two 3-, 4-, 5- or 6-member rings and 1-4 heteroatoms selected from N, O and S.

The present invention also provides a method for treating amyotrophic lateral sclerosis (ALS) by administering to a subject in need thereof a therapeutically effective amount of a pharmaceutical composition comprising a compound of Formula I, II, III, or IV, or a pharmaceutically acceptable salt, ester, hydrate, solvate, prodrug, metabolite, analog or derivative thereof, in combination with a pharmaceutically acceptable excipient, such that ALS is treated.

The present invention also provides a method for alleviating at least one symptom of ALS by administering to a subject in need thereof a therapeutically effective amount of a pharmaceutical composition comprising a compound of Formula I, II, III, or IV, or a pharmaceutically acceptable salt, ester, hydrate, solvate, prodrug, metabolite, analog or derivative thereof. The symptom of ALS may be selected from: twitching, cramping or stiffness of muscles; muscle weakness affecting an arm of a leg; muscle atrophy; slurred and nasal speech; shortness of breath; and difficulty chewing, swallowing or breathing.

The present invention also provides a method for treating ALS, wherein treating ALS comprises prolonging or increasing the survival of the subject suffering from ALS.

The present invention also provides a method for treating ALS, wherein treating ALS comprises reducing cell death or increasing cell survival of a cell from the subject suffering from ALS. In some embodiments, the cell is a motor neuron or an astrocyte.

The present invention also provides a method for treating ALS, further comprising administering at least one second active therapeutic agent. Preferred second active therapeutic agents are selected from the group consisting of riluzole, talampanel (8-methyl-7H-1,3-dioxolo(2,3)benzodiazepine), Tamoxifen, TCH346, Vitamin E, Celecoxib, Creatine, Copaxone, NP001, ozanezumab, Gilenya, SOD1Rx, MC1-186 and combinations thereof.

In one embodiment, the compound is administered at a dosage from about 0.01 to about 50 mg per kg per day.

In one embodiment, the compound is any one of the compounds listed in Table 1. Preferred compounds and pharmaceutical compositions include sodium (4Z,7Z,10R,11E,13E,15Z,17S,19Z)-10,17-dihydroxydocosa-4,7,11,13,15,19-hexaenoate and (4Z,7Z,10R,11E,13E,15Z,17S,19Z)-10,17-dihydroxydocosa-4,7,11,13,15,19-hexaenoic acid.

Preferred routes of administration include intranasal, intracerebroventricular (ICV), and intrathecal administration.

The present invention also provides a pharmaceutical pack or kit comprising one or more containers filled with a compound of Formula I, II, III, or IV, or a pharmaceutically acceptable salt, ester, hydrate, solvate, prodrug, metabolite, analog or derivative thereof in a form suitable for administration.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents, and other references mentioned herein are incorporated by reference. The references cited herein are not admitted to be prior art to the claimed invention. In the case of conflict, the present specification, including definitions, will control. In addition, the materials, methods, and examples are illustrative only and are not intended to be limiting.

Other features and advantages of the invention will be apparent from the following detailed description and claims.

DETAILED DESCRIPTION OF THE INVENTION

1. Docosahexaenoic Acid (DHA) Analogs

Figure 1:
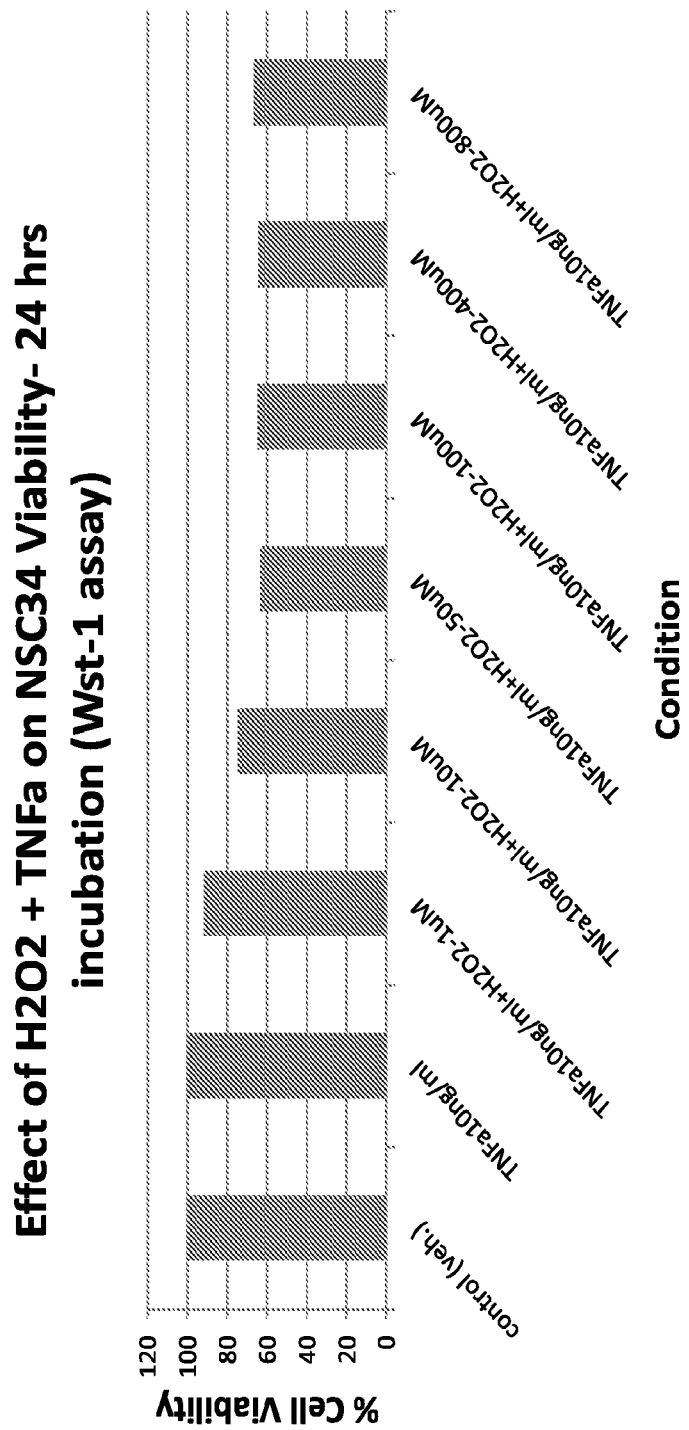
FIG. 1 is a graph depicting the cell viability of NSC34 cells after 24 hours treatment with increasing concentrations of $H_2O_2$ (0-800 μM) and 10 ng/ml TNFα.

The present invention provides DHA analogs or their pharmaceutical compositions for use in the treatment of ALS. In particular, these DHA analogs, (e.g., 10,17-dihydroxyl DHA), including isomers thereof, are isolated or purified from their natural source. Alternatively, these DHA analogs, are artificially synthesized and are optionally further purified.

The present invention relates to the compounds of Formula I:

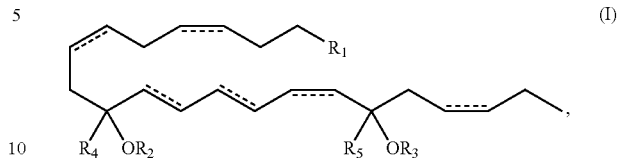

(I)

wherein:

----- represents a cis or trans bond;

$R_1$ is —C(O)O$R_a$, —C(O)N$R_b R_c$, —C(O)H, —C(NH)N$R_b R_c$, —C(S)H, —C(S)O$R_a$, —C(S)N$R_b R_c$, or —CN;

$R_2$ and $R_3$ are each independently H or a protecting group;

$R_4$ and $R_5$ are each independently H, halo, unsubstituted or substituted $C_1$-$C_6$ alkyl, unsubstituted or substituted $C_3$-$C_{10}$ carbocycle, unsubstituted or substituted heterocycle comprising one or two 3-, 4-, 5- or 6-member rings and 1-4 heteroatoms selected from N, O and S, $R_a$ is a protecting group or -$T_1$-$Q_1$;

$R_b$ and $R_c$ are each independently a protecting group or -$T_1$-$Q_1$, or $R_b$ and $R_c$, together with the nitrogen atom to which they are attached, form an unsubstituted or substituted heterocycle comprising one or two 5- or 6-member rings and 1-4 additional heteroatoms selected from N, O and S;

$T_1$ is a bond or unsubstituted or substituted $C_1$-$C_6$ alkyl linker; and $Q_1$ is H, hydroxyl, halogen, unsubstituted or substituted $C_1$-$C_6$ alkyl, unsubstituted or substituted $C_1$-$C_6$ alkoxy, unsubstituted or substituted 2-6 membered heteroalkyl, unsubstituted or substituted $C_3$-$C_{10}$ carbocycle, or unsubstituted or substituted heterocycle comprising one or two 3-, 4-, 5- or 6-member rings and 1-4 heteroatoms selected from N, O and S.

Embodiments of the invention include one or more features below.

For example, the compound used for treating ALS is of Formula II:

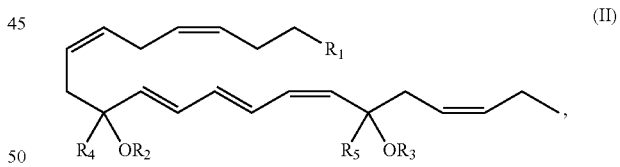

(II)

a pharmaceutically acceptable salt, ester, solvate, hydrate or prodrug thereof.

For example, the compound used for treating ALS is of Formula III:

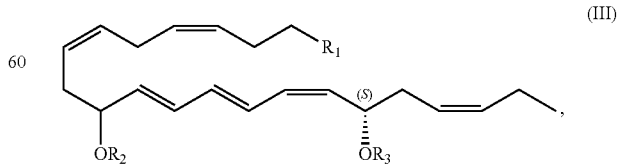

(III)

a pharmaceutically acceptable salt, ester, solvate, hydrate or prodrug thereof.

For example, in Formula I, II, or III, $R_1$ is —C(O)OR$_a$.

For example, $R_a$ is H.

For example, $R_a$ is a protecting group.

For example, in Formula I, II, or III, each of $R_4$ and $R_5$ is H.

For example, at least one of $R_4$ and $R_5$ is substituted or unsubstituted straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl and n-hexyl.

For example, in Formula I, II, or III, each of $R_2$ and $R_3$ is H.

For example, in Formula I, II, or III, at least one of $R_2$ and $R_3$ is a protecting group.

For example, the compound used for treating ALS is 10,17S-dihydroxy-docosa-4Z,7Z,11E,13E,15Z,19Z-hexaenoic acid or a pharmaceutically acceptable salt, ester, solvate, hydrate or prodrug thereof.

For example, the compound used for treating ALS is 10R,17S-dihydroxy-docosa-4Z,7Z,11E,13E,15Z,19Z-hexaenoic acid or a pharmaceutically acceptable salt, ester, solvate, hydrate or prodrug thereof.

For example, the compound used for treating ALS is an isolated compound, e.g., substantially separated from other compounds or isomers that are present in a cellular environment.

For example, the isolated compound used for treating ALS has a purity of at least 75%, 85%, 90, 92.5%, 95%, 97.5%, 99%, 99.5%, or 99.9% by weight.

For example, the isolated compound used for treating ALS is contaminated with at most 25%, 15%, 10%, 7.5%, 5%, 1%, 0.5%, or 0.1% by weight of other isomers of the compound.

For example, the isolated compound used for treating ALS is 10,17S-dihydroxy-docosa-4Z,7Z,11E,13E,15Z,19Z-hexaenoic acid or a pharmaceutically acceptable salt, ester, solvate, hydrate or prodrug thereof.

For example, the isolated compound used for treating ALS is 10R,17S-dihydroxy-docosa-4Z,7Z,11E,13E,15Z,19Z-hexaenoic acid or a pharmaceutically acceptable salt, ester, solvate, hydrate or prodrug thereof.

For example, the isolated compound used for treating ALS is 10R,17S-dihydroxy-docosa-4Z,7Z,11E,13E,15Z,19Z-hexaenoic acid or a pharmaceutically acceptable salt, ester, solvate, hydrate or prodrug thereof, and is contaminated with at most 25%, 15%, 10%, 7.5%, 5%, 1%, 0.5%, or 0.1% by weight of the 10S,17S-enantiomer.

For example, the compound used for treating ALS is an R/S racemate at C-10 carbon atom of the compound.

For example, the compound used for treating ALS is an R/S racemate at C-17 carbon atom of the compound.

For example, the isolated compound used for treating ALS is an R/S racemate at C-10 carbon atom of the compound.

For example, the isolated compound used for treating ALS is an R/S racemate at C-17 carbon atom of the compound.

The compound useful for the method of this invention also includes those of Formula IV:

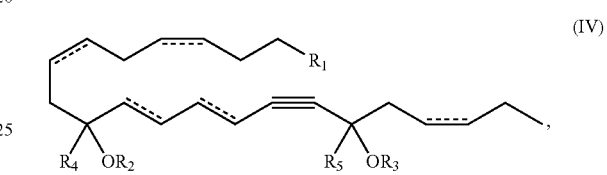

a pharmaceutically acceptable salt, ester, solvate, hydrate or prodrug thereof. In Formula IV, ----- and $R_1$-$R_5$ are defined as above.

For example, the compound of Formula IV is an isolated compound.

Representative compounds useful for the method of the present invention include compounds listed in Table 1.

TABLE 1

| Compound Number | Structure | Name |
|---|---|---|
| 1 | 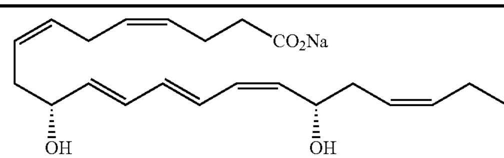 | Sodium 4Z,7Z,10R,11E,13E,15Z,17S,19Z)-10,17-dihydroxydocosa-4,7,11,13,15,19-hexaenoate |
| 2 | 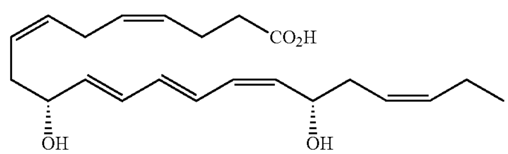 | (4Z,7Z,10R,11E,13E,15Z,17S,19Z)-10,17-dihydroxydocosa-4,7,11,13,15,19-hexaenoic acid |
| 3 | 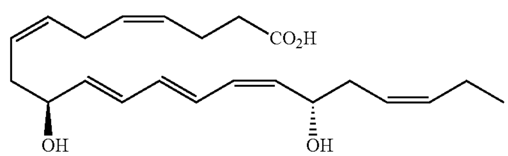 [SMILES: CC/C=C\C[C@H](O)\C=C/C=C/C=C/[C@@H](O)C/C=C\C/C=C\CCC(=O)O] | (4Z,7Z,10S,11E,13E,15Z,17S,19Z)-10,17-dihydroxydocosa-4,7,11,13,15,19-hexaenoic acid |
| 4 | 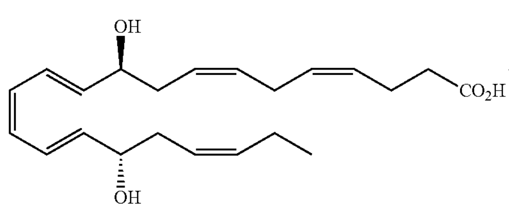 [SMILES: CC/C=C\C[C@H](O)/C=C/C=C\C=C\[C@@H](O)C/C=C\C/C=C\CCC(=O)O] | (4Z,7Z,10S,11E,13Z,15E,17S,19Z)-10,17-dihydroxydocosa-4,7,11,13,15,19-hexaenoic acid |

TABLE 1-continued

| Compound Number | Structure | Name |
|---|---|---|
| 5 | 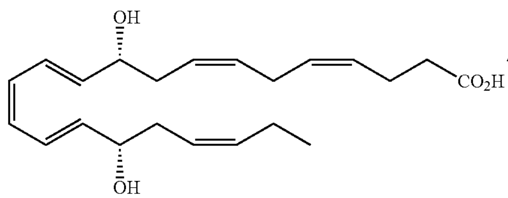 [SMILES: CC/C=C\C[C@H](O)/C=C/C=C\C=C\[C@H](O)C/C=C\C/C=C\CCC(=O)O] | (4Z,7Z,10R,11E,13Z,15E,17S,19Z)-10,17-dihydroxydocosa-4,7,11,13,15,19-hexaenoic acid |
| 6 | 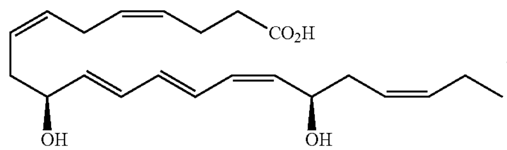 [SMILES: CC/C=C\C[C@@H](O)\C=C/C=C/C=C/[C@@H](O)C/C=C\C/C=C\CCC(=O)O] | (4Z,7Z,10S,11E,13E,15Z,17R,19Z)-10,17-dihydroxydocosa-4,7,11,13,15,19-hexaenoic acid |
| 7 | 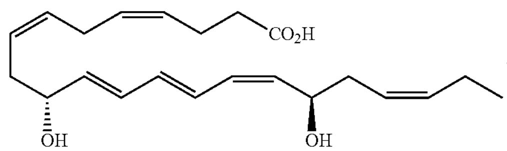 [SMILES: CC/C=C\C[C@@H](O)\C=C/C=C/C=C/[C@H](O)C/C=C\C/C=C\CCC(=O)O] | (4Z,7Z,10R,11E,13E,15Z,17R,19Z)-10,17-dihydroxydocosa-4,7,11,13,15,19-hexaenoic acid |
| 8 | 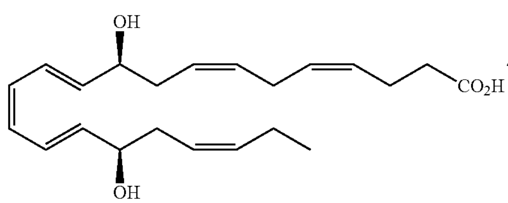 [SMILES: CC/C=C\C[C@@H](O)/C=C/C=C\C=C\[C@@H](O)C/C=C\C/C=C\CCC(=O)O] | (4Z,7Z,10S,11E,13Z,15E,17R,19Z)-10,17-dihydroxydocosa-4,7,11,13,15,19-hexaenoic acid |
| 9 | 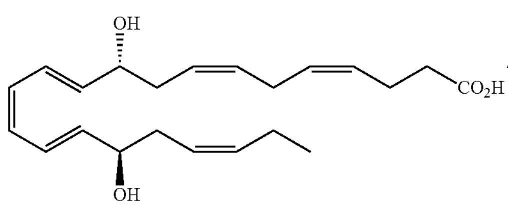 [SMILES: CC/C=C\C[C@@H](O)/C=C/C=C\C=C\[C@H](O)C/C=C\C/C=C\CCC(=O)O] | (4Z,7Z,10R,11E,13Z,15E,17R,19Z)-10,17-dihydroxydocosa-4,7,11,13,15,19-hexaenoic acid |
| 10 | 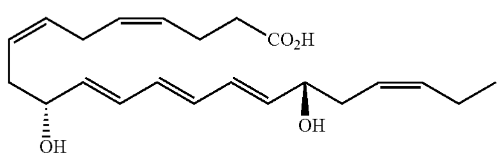 [SMILES: CC/C=C\C[C@H](O)/C=C/C=C/C=C/[C@H](O)C/C=C\C/C=C\CCC(=O)O] | (4Z,7Z,10R,11E,13E,15E,17S,19Z)-10,17-dihydroxydocosa-4,7,11,13,15,19-hexaenoic acid |
| 11 | 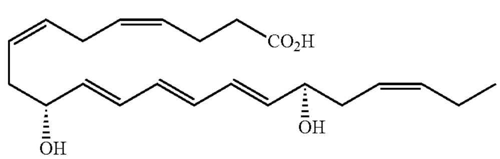 [SMILES: CC/C=C\C[C@@H](O)/C=C/C=C/C=C/[C@H](O)C/C=C\C/C=C\CCC(=O)O] | (4Z,7Z,10R,11E,13E,15E,17R,19Z)-10,17-dihydroxydocosa-4,7,11,13,15,19-hexaenoic acid |
| 12 | 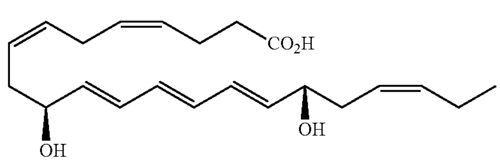 [SMILES: CC/C=C\C[C@H](O)/C=C/C=C/C=C/[C@@H](O)C/C=C\C/C=C\CCC(=O)O] | (4Z,7Z,10S,11E,13E,15E,17S,19Z)-10,17-dihydroxydocosa-4,7,11,13,15,19-hexaenoic acid |
| 13 | 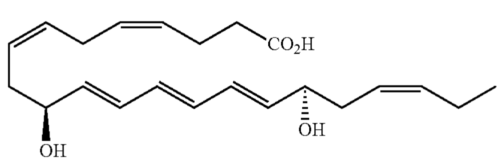 [SMILES: CC/C=C\C[C@@H](O)/C=C/C=C/C=C/[C@@H](O)C/C=C\C/C=C\CCC(=O)O] | (4Z,7Z,10S,11E,13E,15E,17R,19Z)-10,17-dihydroxydocosa-4,7,11,13,15,19-hexaenoic acid |

TABLE 1-continued

| Compound Number | Structure | Name |
|---|---|---|
| 14 | 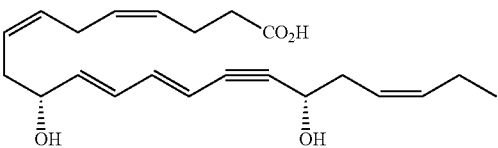 [SMILES: CC/C=C\C[C@H](O)C#C/C=C/C=C/[C@H](O)C/C=C\C/C=C\CCC(=O)O] | (4Z,7Z,10R,11E,13E,17S,19Z)-10,17-dihydroxydocosa-4,7,11,13,19-pentaen-15-ynoic acid |

The compounds that can be used for treating ALS also include those omega-3 polyunsaturated fatty acid such as eicosapentaenoic acid (EPA), DHA, and their analogs (e.g., di-/tri-hydroxyl EPA or DHA) described in U.S. Pat. Nos. 7,759,395, 7,782,152, and 7,709,669, US 2009/0156673, and WO 2010/091226. Compound 1 in Table 1 is also referred to herein as NPD1.

As used herein, the term "isolated compound" refers to the subject compound being purified, e.g., substantially separated from other compounds or isomers that are present in a cellular environment where resolvins are produced or that are present in crude products of synthetic chemical manufacturing processes. In certain embodiments, a purified compound is contaminated with less than 25%, less than 15%, less than 10%, less than 5%, less than 2%, or even less than 1% of cellular components (proteins, nucleic acids, carbohydrates, etc.), chemical byproducts, reagents, and starting materials, and the like. In certain embodiments, a purified compound is contaminated with less than 25%, less than 15%, less than 10%, less than 5%, less than 2%, or even less than 1% of other resolvins and/or other isomers of the compound. The addition of pharmaceutical excipients, other active agents, or other pharmaceutically acceptable additives is not understood to decrease the purity of a compound as this term is used herein.

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

"Heteroalkyl" groups are alkyl groups, as defined above, that have an oxygen, nitrogen, sulfur or phosphorous atom replacing one or more hydrocarbon backbone carbon atoms.

As used herein, the term "cycloalkyl", "$C_3$, $C_4$, $C_5$, $C_6$, $C_7$ or $C_8$ cycloalkyl" or "$C_3$-$C_8$ cycloalkyl" is intended to include hydrocarbon rings having from three to eight carbon atoms in their ring structure. In one embodiment, a cycloalkyl group has five or six carbons in the ring structure.

The term "substituted alkyl" refers to alkyl moieties having substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)).

Unless the number of carbons is otherwise specified, "lower alkyl" includes an alkyl group, as defined above, having from one to six, or in another embodiment from one to four, carbon atoms in its backbone structure. "Lower alkenyl" and "lower alkynyl" have chain lengths of, for example, two to six or of two to four carbon atoms.

As used herein, "alkyl linker" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl linker is intended to include $C_1$, $C_2$, $C_3$, $C_4$, $C_5$ and $C_6$ alkyl linker groups. Examples of alkyl linker include, moieties having from one to six carbon atoms, such as, but not limited to, methyl (—CH$_2$—), ethyl (—CH$_2$CH$_2$—), n-propyl (—CH$_2$CH$_2$CH$_2$—), i-propyl (—CHCH$_3$CH$_2$—), n-butyl (—CH$_2$CH$_2$CH$_2$CH$_2$—), s-butyl (—CHCH$_3$CH$_2$CH$_2$—), i-butyl (—C(CH$_3$)$_2$CH$_2$—), n-pentyl (—CH$_2$CH$_2$CH$_2$CH$_2$CH$_2$—), s-pentyl (—CHCH$_3$CH$_2$CH$_2$CH$_2$—) or n-hexyl (—CH$_2$CH$_2$CH$_2$CH$_2$CH$_2$CH$_2$—).

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), branched alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. In certain embodiments, a straight chain or branched alkenyl group has six or fewer carbon atoms in its backbone (e.g., $C_2$-$C_6$ for straight chain, $C_3$-$C_6$ for branched chain). Likewise, cycloalkenyl groups may have from five to eight carbon atoms in their ring structure, and in one embodiment, cycloalkenyl groups have five or six carbons in the ring structure. The term "$C_2$-$C_6$" includes alkenyl groups containing two to six carbon atoms. The term "$C_3$-$C_6$" includes alkenyl groups containing three to six carbon atoms.

"Heteroalkenyl" includes alkenyl groups, as defined herein, having an oxygen, nitrogen, sulfur or phosphorous atom replacing one or more hydrocarbon backbone carbons.

The term "substituted alkenyl" refers to alkenyl moieties having substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), branched alkynyl groups, and cycloalkyl or cycloalkenyl substituted alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

"Heteroalkynyl" includes alkynyl groups, as defined herein, having an oxygen, nitrogen, sulfur or phosphorous atom replacing one or more hydrocarbon backbone carbons.

The term "substituted alkynyl" refers to alkynyl moieties having substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aryl" includes groups with aromaticity, including "conjugated", or multicyclic, systems with at least one aromatic ring. Examples include phenyl, benzyl, etc.

"Heteroaryl" groups are aryl groups, as defined above, having from one to four heteroatoms in the ring structure, and may also be referred to as "aryl heterocycles" or "heteroaromatics". As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and S(O)$_p$, where p=one or two). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthridine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The aryl or heteroaryl aromatic ring can be substituted at one or more ring positions with such substituents as described above, for example, alkyl, alkenyl, akynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

As used herein, "carbocycle" or "carbocyclic ring" is intended to include any stable monocyclic, bicyclic or tricyclic ring having the specified number of carbons, any of which may be saturated, unsaturated, or aromatic. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, [4.4.0]bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" includes any ring structure (saturated or partially unsaturated or aromatic) which contains at least one ring heteroatom (e.g., N, O or S). Examples of heterocycles include, but are not limited to, morpholine, pyrrolidine, tetrahydrothiophene, piperidine, piperazine and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted", as used herein, means that any one or more hydrogen atmos on the designated atom is replaced with a selection from the indicated groups, provided that the designated atom's normal valency is not exceeded, and that the substitution results in a stable compound. When a substituent is keto or oxo (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R_1$ at each occurrence is selected independently from the definition of $R_1$. Also, combinations of substituents and/or variables are permissible, but only if such combinations result in stable compounds.

The term "hydroxy" or "hydroxyl" includes groups with an —OH or —O⁻.

As used herein, "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

The term "carbonyl" or "carboxy" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

"Acyl" includes moieties that contain the acyl radical (—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aroyl" includes moieties with an aryl or heteroaromatic moiety bound to a carbonyl group. Examples of aroyl groups include phenylcarboxy, naphthyl carboxy, etc.

"Alkoxyalkyl", "alkylaminoalkyl" and "thioalkoxyalkyl" include alkyl groups, as described above, wherein oxygen, nitrogen or sulfur atoms replace one or more hydrocarbon backbone carbon atoms.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ether" or "alkoxy" includes compounds or moieties which contain an oxygen atom bonded to two carbon atoms or heteroatoms. For example, the term includes "alkoxyalkyl", which refers to an alkyl, alkenyl, or alkynyl group covalently bonded to an oxygen atom which is covalently bonded to an alkyl group.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The term "thiocarbonyl" or "thiocarboxy" includes compounds and moieties which contain a carbon connected with a double bond to a sulfur atom.

The term "thioether" includes moieties which contain a sulfur atom bonded to two carbon atoms or heteroatoms. Examples of thioethers include, but are not limited to alkthioalkyls, alkthioalkenyls and alkthioalkynyls. The term "alkthioalkyls" include moieties with an alkyl, alkenyl or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

As used herein, "amine" or "amino" includes moieties where a nitrogen atom is covalently bonded to at least one carbon or heteroatom. "Alkylamino" includes groups of compounds wherein nitrogen is bound to at least one alkyl group. Examples of alkylamino groups include benzylamino, methylamino, ethylamino, phenethylamino, etc. "Dialkylamino" includes groups wherein the nitrogen atom is bound to at least two additional alkyl groups. Examples of dialkylamino groups include, but are not limited to, dimethylamino and diethylamino. "Arylamino" and "diarylamino" include groups wherein the nitrogen is bound to at least one or two aryl groups, respectively. "Alkylarylamino", "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

The term "amandine" or "amidinyl" includes compounds or moietyies having the general structure of —C(=NR)NR'R", N(R'R")—CR(=N)—, or CR'(=NR)NR"—, in which R, R', and R" can each independently be H, alkyl, cycloalkyl, cycloalkenyl, heterocycle, aryl, or heteroaryl etc. One example of amidinyl is —C(=NH)NH$_2$. Amidines can be substituted with substituents such as straight chain alkyl, branched alkyl, cycloalkyl, aryl, heteroaryl or heterocycle. Substituents on amide groups may be further substituted.

Compounds of the present invention that contain nitrogens can be converted to N-oxides by treatment with an oxidizing agent (e.g., 3-chloroperoxybenzoic acid (m-CPBA) and/or hydrogen peroxides) to afford other compounds of the present invention. Thus, all shown and claimed nitrogen-containing compounds are considered, when allowed by valency and structure, to include both the compound as shown and its N-oxide derivative (which can be designated as N→O or N$^+$—O$^-$). Furthermore, in other instances, the nitrogens in the compounds of the present invention can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

In the present specification, the structural formula of the compound represents a certain isomer for convenience in some cases, but the present invention includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present invention. Furthermore, so-called metabolite which is produced by degradation of the present compound in vivo is included in the scope of the present invention.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four nonidentical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this invention include all atropic isomers thereof.

"Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine.

It is to be understood that the compounds of the present invention may be depicted as different tautomers. It should also be understood that when compounds have tautomeric forms, all tautomeric forms are intended to be included in the scope of the present invention, and the naming of the compounds does not exclude any tautomer form.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds represented by Formula I are 10,17-dihydroxyl DHA derivatives, and have Formula I as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, Chem. Rev. 96, 3147-3176, 1996.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

"Protecting group": as used herein, means that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, certain exemplary oxygen protecting groups may be utilized. These oxygen (or hydroxyl) protecting groups include, but are not limited to methyl ethers, substituted methyl ethers (e.g., MOM (methoxymethyl ether), MTM (methylthiomethyl ether), BOM (benzyloxymethyl ether), and PMBM (p-methoxybenzyloxymethyl ether)), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, and TBDPS (t-butyldiphenyl silyl ether), esters (e.g., formate, acetate, benzoate (Bz), trifluoroacetate, and dichloroacetate), carbonates, cyclic acetals and ketals, and glycol ethers, such as ethylene glycol and propylene glycol derivatives and allyl ethers. In certain other exemplary embodiments, nitrogen protecting groups are utilized. Nitrogen protecting groups, as well as protection and deprotection methods are known in the art. Nitrogen protecting groups include, but are not limited to, carbamates (including methyl, ethyl and substituted ethyl carbamates (e.g., Troc), amides, cyclic imide derivatives, N-Alkyl and N-Aryl amines, imine derivatives, and enamine derivatives, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitroveratryloxycarbonyl ("NVOC") and the like. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

2. Synthesis of 10,17-Dihydroxyl DHA Compounds

The present disclosure provides methods for the synthesis of the compounds of Formula I-IV.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups; therefore various substituted starting materials can be used. The processes generally provide the desired final compound at or near the end of the overall process, although it may be desirable in certain instances to further convert the compound to a pharmaceutically acceptable salt, ester or prodrug thereof.

Compounds of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, 5$^{th}$ edition, John Wiley & Sons: New York, 2001; and Greene, T. W., Wuts, P. G. M., *Protective Groups in Organic Synthesis*, 3$^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present invention.

Compounds of the present invention can be conveniently prepared by a variety of methods familiar to those skilled in the art. The compounds of this invention with Formulae I-IV may be prepared according to the following Scheme from commercially available starting materials or starting materials which can be prepared using literature procedures. These procedures show the preparation of representative compounds of this invention.

Scheme 1
One general procedure is illustrated below.

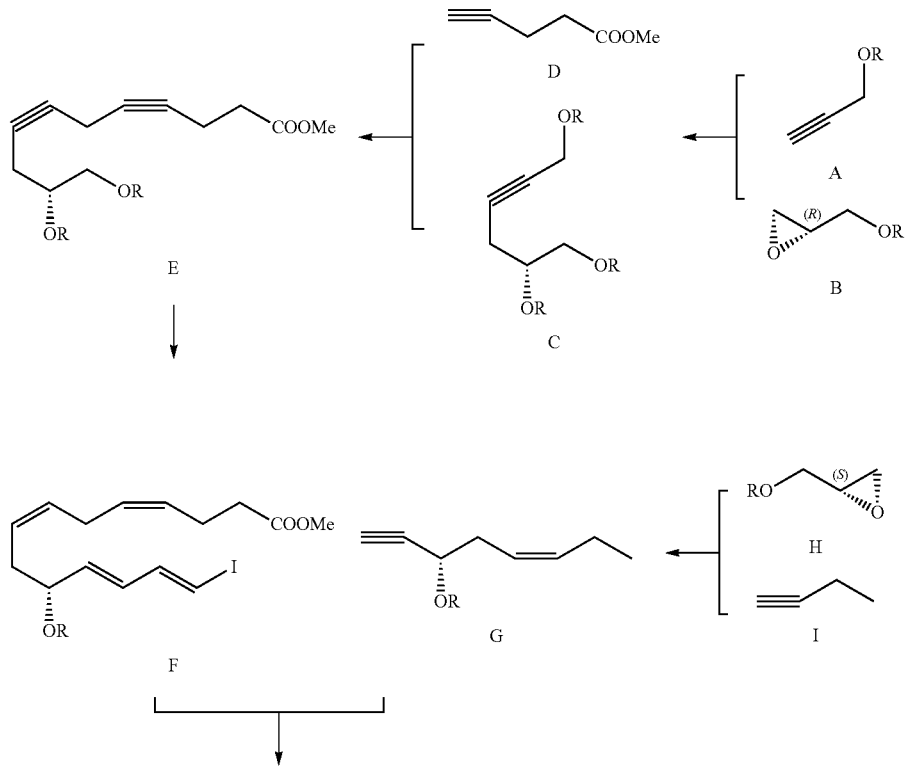

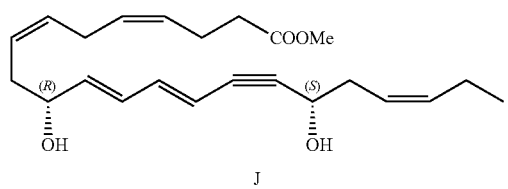

J

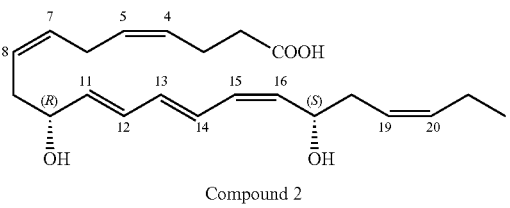

Compound 2

Scheme 1 above demonstrates strategy for total synthesis of Compound 2 and related isomers. The C-10 and C-17 stereochemistry of Compound 2 is derived from enantiomerically pure glycidol derivatives B and H which are reacted with alkynyl nucleophiles derived from A and I, respectively. The (Z) alkene geometry at positions 4-5, 7-8, 15-16 and 19-20 was obtained from selective hydrogenation of acetylenic precursors, which were constructed using coupling procedures. The (E) geometry at positions 11-12 and 13-14 was secured during the synthesis of intermediate F. Other stereoisomers of Compound 2 can be synthesized similarly.

Each of the stereocontrolled steps from defined precursors enabled preparation of geometric isomers of the conjugated triene region that were confirmed by NMR (see US Publication No. 2009/0156673).

3. Methods of Treatment

The present invention provides methods for treating ALS in a subject in need thereof by administering to a subject in need of such treatment, a therapeutically effective amount of a compound described herein, or a pharmaceutically acceptable salt, prodrug, metabolite, polymorph or solvate thereof. The present invention further provides the use of a compound described herein, or a pharmaceutically acceptable salt, prodrug, metabolite, polymorph or solvate thereof, for the preparation of a medicament useful for the treatment of ALS.

The present invention provides methods for alleviating or ameliorating at least one symptom of ALS in a subject in need thereof by administering to a subject in need of such treatment, a therapeutically effective amount of a compound described herein, or a pharmaceutically acceptable salt, prodrug, metabolite, polymorph or solvate thereof. Symptoms of ALS include twitching, cramping or stiffness of muscles; muscle weakness affecting an arm of a leg; muscle atrophy; slurred and nasal speech; shortness of breath; and difficulty chewing, swallowing or breathing. The present invention further provides the use of a compound described herein, or a pharmaceutically acceptable salt, prodrug, metabolite, polymorph or solvate thereof, for the preparation of a medicament useful for ameliorating at least one symptom of ALS.

The present invention provides methods for alleviating or ameliorating at least one clinical sign of ALS in a subject in need thereof by administering to a subject in need of such treatment, a therapeutically effective amount of a compound described herein, or a pharmaceutically acceptable salt, prodrug, metabolite, polymorph or solvate thereof. The present invention further provides the use of a compound described herein, or a pharmaceutically acceptable salt, prodrug, metabolite, polymorph or solvate thereof, for the preparation of a medicament useful for ameliorating at least one clinical sign of ALS.

The present invention provides methods for prolonging or increasing the survival of a subject suffering from, or diagnosed with, ALS by administering to a subject in need of such treatment, a therapeutically effective amount of a compound described herein, or a pharmaceutically acceptable salt, prodrug, metabolite, polymorph or solvate thereof. The present invention further provides the use of a compound described herein, or a pharmaceutically acceptable salt, prodrug, metabolite, polymorph or solvate thereof, for the preparation of a medicament useful for prolonging or increasing the survival of a subject suffering from, or diagnosed with, ALS.

The present invention provides methods for preventing, or delaying the onset of, ALS in a subject at risk thereof by administering to a subject in need of such treatment, a therapeutically effective amount of a compound described herein, or a pharmaceutically acceptable salt, prodrug, metabolite, polymorph or solvate thereof. The present invention further provides the use of a compound described herein, or a pharmaceutically acceptable salt, prodrug, metabolite, polymorph or solvate thereof, for the preparation of a medicament useful for prolonging or increasing the survival of a subject suffering from, or diagnosed with, ALS.

The present invention also provides a method for reducing or inhibiting cell death by contacting a cell with a compound of Formula I, II, III, or IV, or a pharmaceutically acceptable salt, ester, hydrate, solvate, prodrug, metabolite, analog or derivative thereof. The present invention also provides a method for increasing cell survival or cell viability by contacting a cell with a compound of Formula I, II, III, or IV, or a pharmaceutically acceptable salt, ester, hydrate, solvate, prodrug, metabolite, analog or derivative thereof. The cell is a motor neuron or an astrocyte.

Amyotrophic lateral sclerosis (ALS), also known under the name of Charcot's disease and Lou Gehrig's disease, is a fatal disease resulting from the degeneration of motor neurones and corticospinal tracts. With an incidence at present of 2.5/100,000 and, constantly on the increase, a prevalence of 6-10/100,000, ALS affects 90,000 people in the developed countries, for the most part adults who are still young (between 50 and 60). The disease is accompanied by progressive paralysis, leading to the total loss of motor and respiratory functions and then to death with a delay of two to eight years after the appearance of the first symptoms (three years on average). The cardinal feature of ALS is the loss of spinal motor neurons, which causes the muscles under their control to weaken and waste away leading to paralysis. Thus, one of the key characteristics is the progressive loss of muscle strength.

Early symptoms of ALS include increasing muscle weakness, particularly in the arms and legs, and in the muscles associated with speech, swallowing and breathing. Symptoms of weakness and muscle atrophy usually begin asymmetrically and distally in one limb, and then spread within the neuroaxis to involve contiguous groups of motor neurons. Symptoms can begin either in bulbar or limb muscles. Clinical signs of both lower and upper motor neuron involvement are required for a definitive diagnosis of ALS. ALS diagnosis is based on the El Escorial criteria revised mainly on clinical and electrophysiological findings in four body regions (Brooks et al., *Amyotroph. Lateral Scler. Other Motor Neuron Disord.*, 1: 293-299, 2000). Respiration is usually affected late in limb onset patients, but occasionally can be an early manifestation in patients with bulbar onset symptoms. The most typical feature of this progressive lethal disease is the degeneration of cortical, bulbar and spinal motor neurons, except for the neurons that control the bladder, and the oculomotor neurons. This leads to muscle weakness, fasciculations, muscle atrophy, speech and swallowing disabilities, progressive paralysis, and death caused by respiratory failure.

Clinical signs of ALS are known in the art. The term "clinical sign" as used herein refers to an objective indication of some medical fact or characteristic of ALS that can be objectively measured or quantified. A clinical sign may be detected by a physician during a physical examination or by a clinical scientist by means of an in vitro examination of a sample from a patient. A clinical sign of ALS may also be a symptom of ALS, wherein the symptom of ALS can be objectively measured. Other clinical signs of ALS may include changes in expression or levels of particular biomarkers that are known to be involved in ALS pathology. The presence, absence, or modulation of biomarker mRNA or protein expression can be measured from biological samples using methods known in the art, such as nucleic acid amplification and immunoassay techniques. Biological samples from the patient may be blood or cerebrospinal fluid samples. Clinical signs characterized by abnormal cell or tissue activity can be captured using bioimaging methods known in the art, such as MRI (magnetic resonance imaging), EMG (electromyography), and PET (positron emission tomography). For example, changes in microglial activity can be measured by bioimaging, such as capture by PET and known ligands. It is well known in the art that microglial cells of the pro-inflammatory type (M1) are upregulated in ALS, and correlations between increased M1 activity and ALS disease severity have been established. Thus, measured reduction of M1 activity indicates the alleviation of a clinical sign of ALS.

The disease was first described in 1869 by the French neurobiologist and physician Jean-Martin Charcot who linked the symptoms of ALS to a group of nerves specifically affected by the disease; the motor neurons that originate in the spinal cord. The name of the disease reflects the different tissue compartments that are severely affected. In particular, "amyotrophic" refers to the atrophy of muscle fibers and loss of muscle mass; "lateral" refers to the nerve tracks that run down both sides of the spinal cord, where many neurons affected by ALS are found; and "sclerosis" refers to the scar tissue that remains following degeneration of the nerves.

The defining feature of ALS is the death and loss of both upper and lower motor neurons in the motor cortex of the brain, the brain stem, and the spinal cord. Prior to their destruction, motor neurons develop proteinaceous inclusions in their cell bodies and axons. This may be partly due to defects in protein degradation. These inclusions often contain ubiquitin, and generally incorporate one of the ALS-associated proteins: SOD1, TAR DNA binding protein (TDP-43, or TARDBP), or FUS. The role of astrocytes in the etiology of disease progression is not well understood, with many studies arguing a beneficial role for astrocytes and with other studies suggesting a detrimental role.

ALS has both familial (5-10%) and sporadic forms (90-95%). The physio-pathological origin of the sporadic forms of ALS remains unknown. Several hypotheses have been proposed. The motor neurons degeneration could result from an alteration in the metabolism of glutamate leading to an increase in the concentration of this excitatory amino acid in the motor cortex and the spinal cord, which is commonly referred to as excitotoxicity. The possibility of inflammatory components has likewise been put forward on the basis of either increased microglial activity, or the presence of autoantibody against the voltage-sensitive calcium channels in certain patients. Another possibility is misfolding of proteins with secondary pathological gain-of-function. The implication of environmental factors such as exposure to certain viruses, or to aluminium is likewise possible.

The studies bearing on the hereditary forms of ALS have allowed it to be shown that point mutations in the gene for cupro-zinc containing superoxide dismutase (SOD), localized on the 21q22-1 chromosome, are responsible for the pathology in 20% of the familial forms. These mutations do not cause reduction of the dismutase activity of the SOD. The mutated enzymes produce potentially cytotoxic hydroxyl radicals which are not produced by the wild-type SOD.

Additional studies have shown that mutations in superoxide dismutase-1 (SOD1) and/or other genes and environmental factors may be responsible for the activation of the pathogenic mechanisms that lead to ALS. Several pathogenic mechanisms have been proposed. (1) Glutamate-induced excitotoxicity: overstimulation of neurons by glutamate causes the accumulation of calcium ions in cellular compartments, which leads to activation of apoptotic pathways; (2) Oxidative stress that is caused by an imbalance between the production of reactive oxygen species and antioxidant defenses; (3) Protein aggregation: oxidative stress and mitochondrial alteration could be responsible for protein aggregation; mutant SOD1 protein or other ALS-related genes tend to be misfolded or form aggregates that, in turn, trigger a toxic cascade that leads to neuronal degeneration; (4) Mitochondrial dysfunction, which leads to oxidative stress, decreased activity of respiratory complexes, decreased ATP levels and cytochrome c release; (5) Deficit in neurotrophic growth factors, including insulin-like growth factor 1, and activation of proteolytic systems; (6) Impaired axonal transport; (7) Neurofilament aggregation; (8) Inflammatory dysfunction and contribution of non-neuronal cells; and/or (9) genetic factors.

As used herein, the term "ALS" includes all of the classifications of ALS known in the art, including, but not limited to classical ALS (typically affecting both lower and upper motor neurons), Primary Lateral Sclerosis (PLS, typically affecting only the upper motor neurons), Progressive Bulbar Palsy (PBP or Bulbar Onset, a version of ALS that typically begins with difficulties swallowing, chewing and speaking), Progressive Muscular Atrophy (PMA, typically affecting only the lower motor neurons) and familial ALS (a genetic version of ALS). The term "ALS" does not include neurodegenerative disorders such as multiple sclerosis, Huntington's disease, Parkinson's disease or Alzheimer's disease. Thus, the methods of the present invention do not comprise the treatment of multiple sclerosis, Huntington's disease, Parkinson's disease or Alzheimer's disease.

As used herein, a "subject in need thereof" is a subject having ALS, or a subject having an increased risk of developing ALS relative to the population at large. Preferably, a subject in need thereof has ALS. A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

As used herein, "candidate compound" refers to a compound of the present invention, or a pharmaceutically acceptable salt, prodrug, metabolite, polymorph or solvate thereof.

As used herein, "monotherapy" refers to the administration of a single active or therapeutic compound to a subject in need thereof. Preferably, monotherapy will involve administration of a therapeutically effective amount of an active compound.

For example, ALS monotherapy with one of the compound of the present invention, or a pharmaceutically acceptable salt, prodrug, metabolite, analog or derivative thereof, to a subject in need of treatment of ALS. Monotherapy may be contrasted with combination therapy, in which a combination of multiple active compounds is administered, preferably with each component of the combination present in a therapeutically effective amount. In one aspect, monotherapy with a compound of the present invention, or a pharmaceutically acceptable salt, prodrug, metabolite, polymorph or solvate thereof, is more effective than combination therapy in inducing a desired biological effect.

As used herein, "treating" or "treat" describes the management and care of a patient for the purpose of combating a disease, condition, or disorder and includes the administration of a compound of the present invention, or a pharmaceutically acceptable salt, prodrug, metabolite, polymorph or solvate thereof, to alleviate the symptoms or complications of a disease, condition or disorder, or to eliminate the disease, condition or disorder.

A compound of the present invention, or a pharmaceutically acceptable salt, prodrug, metabolite, polymorph or solvate thereof, can also be used to prevent a disease, condition or disorder. The term "preventing" or "prevent" as used herein includes either preventing the onset of a clinically evident disease progression altogether or preventing or slowing the onset of a preclinically evident stage of a disease in individuals at risk. This includes prophylactic treatment of those at risk of developing a disease.

As used herein, the term "alleviate" or "ameliorate" is meant to describe a process by which the severity of a sign or symptom of a disorder is decreased. Importantly, a sign or symptom can be alleviated without being eliminated. In a preferred embodiment, the administration of pharmaceutical compositions of the invention leads to the elimination of a sign or symptom, however, elimination is not required. Therapeutically effective dosages are expected to decrease the severity of a sign or symptom.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

As used herein, "combination therapy" or "co-therapy" includes the administration of a compound of the present invention, or a pharmaceutically acceptable salt, prodrug, metabolite, polymorph or solvate thereof, and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations of the present invention.

"Combination therapy" is intended to embrace administration of these therapeutic agents in a sequential manner, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or physical therapy). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

A compound of the present invention, or a pharmaceutically acceptable salt, prodrug, metabolite, analog or derivative thereof, may be administered in combination with a second active therapeutic agent. Second active therapeutic agents include but are not limited to neurotrophic growth factors, anti-oxidants (e.g., coenzyme $Q_{10}$, manganoporphyrin, AEOL 10150, KNS-760704 [(6R)-4,5,6,7-tetrahydro-N6-propyl-2,6-benzothiazole-diamine dihydrochloride, RPPX], Edaravone (3-methyl-1-phenyl-2-pyrazolin-5-one, MCI-186)), anti-inflammatory agents (e.g., TNF-α, Celastrol), histone deacetylase (HDAC) inhibitors (e.g., Valproic acid (VPA), TCH346 (Dibenzo(b,f)oxepin-10-ylmethyl-methylprop-2-ynylamine), minocycline, Tauroursodeoxycholic Acid), NMDA receptor antagonists (e.g., Memantine), heat shock protein inducers (such as Arimoclomol), autophage inducers (e.g., rapamycin, lithium), cephalosporins (e.g., Cefatriaxone), microRNA, or combinations thereof.

As used herein, microRNA (or miRNA or miR) is small, non-coding, RNA molecules (length 19-25 nucleotides). For example, miR-1, miR-133, miR-214, miR-181 and miR-206.

Additional second active therapeutic agents which can be used in combination with the compounds of the present invention include, but are not limited to, riluzole, talampanel (8-methyl-7H-1,3-dioxolo(2,3)benzodiazepine), Tamoxifen, TCH346, Vitamin E, Celecoxib, Creatine, Copaxone, NP001, ozanezumab, Gilenya, SOD1Rx, MC1-186 or combinations thereof.

The trophic growth factors used in the context of the invention are essentially classed under three families: the neurotrophin family, the neurokine family and the TGF beta family. Growth factors include, but are not limited to, insulin-like growth factor (IGF-1), nerve growth factor (NGF), glial-cell-line-derived neurotrophic factor (GDNF), vascular endothelial growth factor (VEGF), $VEGF_{165}$, fibroblast growth factor (FGF), ciliary neurotrophic factor (CNTF), glial cell-derived neurotrophic factor (GDNF), transforming growth factors (TGF-α, TGF-β), neurotrophin 3 (NT3), neurotrophin 4/5 (NT4/5), brain-derived neurotrophic factor (BDNF), hepatocyte growth factor (HGF), bone morphogenetic proteins (BMPs), erythropoietin (EPO), thrombopoietin (TPO), granulocyte-colony stimulating factor (G-CSF), or combinations thereof.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., $18^{th}$ edition (1990). These texts can, of course, also be referred to in making or using an aspect of the invention.

4. Pharmaceutical Compositions

The present invention also provides pharmaceutical compositions comprising a compound of Formulae I-IV in combination with at least one pharmaceutically acceptable excipient or carrier, for use in the treatment, amelioration, or prevention of ALS.

A "pharmaceutical composition" is a formulation containing the compounds of the present invention in a form suitable for administration to a subject.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the invention is formulated to be compatible with its intended route of administration. A variety of routes are contemplated, including but not limited to, oral, pulmonary, rectal, parenteral, intradermal, transdermal, topical, transmucosal, subcutaneous, intravenous, intramuscular, intraperitoneal, inhalational, buccal, sublingual, intrapleural, intracerebroventricular (ICV), intrathecal, intranasal, and the like.

Solutions or suspensions used for the appropriate delivery can include the following components: a sterile diluent such as water for injection, saline solution, fixed oils, polyethylene glycols, glycerine, propylene glycol, polysorbate, tocopherol polyethylene glycol succinate (TPGS), or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. These preparations can be enclosed in ampoules, disposable syringes or multiple dose vials made of glass or plastic.

A compound or pharmaceutical composition thereof can be administered to a subject in many of the well-known methods currently used for ALS treatment. Preferably, administration is a continuous infusion and includes the continuous subcutaneous delivery via an osmotic minipump. Individuals suffering ALS with bulbar onset can benefit more from ICV or intrathecal delivery of a compound of the present invention at the cervical level, while ALS patients with lumbar onset can benefit more from an intrathecal infusion of a compound of the present invention at the spinal/lumbar level. Preferably, a compound of the present invention is delivered directly into the cerebrospinal fluid (CSF). A compound of the present invention can be continuously administered close to the place of onset. Preferably, close to the onset administration is an intrathecal administration. Intrathecal administration can for example be performed by means of surgically implanting a pump and running a catheter to the spine or a brain ventricle. Preferred administration is by continuous intrathecal delivery.

In general, a suitable daily dose of a compound of the invention will be that amount of the compound which is the lowest dose effective to produce a therapeutic effect. Such an effective dose will generally depend upon the factors described above. Generally, intravenous and subcutaneous doses of the compounds of this invention for a patient, when used for the indicated therapeutic effects, will range from about 0.0001 to about 100 mg per kilogram of body weight per day, more preferably from about 0.01 to about 50 mg per kg per day, and still more preferably from about 0.1 to about 40 mg per kg per day. For example, between about 0.01 microgram and 20 micrograms, between about 20 micrograms and 100 micrograms and between about 10 micrograms and 200 micrograms of the compounds of the invention are administered per 20 grams of subject weight. Generally, intrathecal or ICV doses of the compounds of this invention for a patient, when used for the indicated therapeutic effects, will range from about 0.0001 μg to about 10 mg per kilogram of body weight per day, more preferably from about 0.001 μg to about 5 mg per kg per day, and still more preferably from about 0.01 μg to about 4 mg per kg per day. For example, between about 0.01 nanogram and 2 micrograms, between about 20 nanograms and 10 micrograms and between about 10 nanograms and 20 micrograms of the compounds of the invention are administered per 20 grams of subject weight.

If desired, the effective daily dose of the active compound may be administered as two, three, four, five, six or more sub-doses administered separately at appropriate intervals throughout the day, optionally, in unit dosage forms.

The pharmaceutical compositions of the invention include a "therapeutically effective amount" or a "prophylactically effective amount" of one or more of the compounds of the invention. A "therapeutically effective amount" refers to an amount effective, at dosages and for periods of time necessary, to achieve the desired therapeutic result, e.g., a diminishment or prevention of effects associated with various disease states or conditions. A therapeutically effective amount of the compound may vary according to factors such as the disease state, age, sex, and weight of the individual, and the ability of the therapeutic compound to elicit a desired response in the individual. A therapeutically effective amount is also one in which any toxic or detrimental effects of the therapeutic agent are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of a compound of the invention is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result ameliorating at least one symptom of ALS (e.g., in slowing, and preferably regressing, the degeneration of upper and lower neurons) and also preferably causing complete regression of ALS. An effective amount of a pharmaceutical agent is that which provides an objectively identifiable improvement as noted by the clinician or other qualified observer. As used herein, the term "dosage effective manner" refers to amount of an active compound to produce the desired biological effect in a subject or cell.

For any compound, the therapeutically effective amount can be estimated initially either in cell culture assays, e.g., brain or central nervous system cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

In one embodiment, the pharmaceutical composition is in bulk or in unit dosage form. The unit dosage form is any of a variety of forms, including, for example, a solution, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including but not limited to, oral, pulmonary, rectal, parenteral, intradermal, transdermal, topical, transmucosal, subcutaneous, intravenous, intramuscular, intraperitoneal, inhalational, buccal, sublingual, intrapleural, intracerebroventricular (ICV), intrathecal, intranasal, and the like.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers or propellants that are required.

The pharmaceutical compositions can be included in a container, pack, or dispenser together with instructions for administration.

The compounds of the present invention are capable of further forming salts. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The compounds of the present invention can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., an acetate, propionate or other ester.

The compounds of the present invention can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs in the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the invention, and the like, See Bundegaard, H., *Design of Prodrugs*, p 1-92, Elesevier, New York-Oxford (1985).

The compounds, or pharmaceutically acceptable salts, esters or prodrugs thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Techniques for formulation and administration of the disclosed compounds of the invention can be found in *Remington: the Science and Practice of Pharmacy*, 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

EXAMPLES

Example 1

In Vitro Activity Assay

It is well-known in the art that inflammation and oxidative stress are significant contributors to neurodegeneration. $H_2O_2$ is commonly used in experiments to simulate oxidate stress. Furthermore, in ALS models, increases in TNF-alpha have been reported, indicating that TNF-alpha as a relevant stressor. Accordingly, in this in vitro assay, TNF-alpha and hydrogen peroxide ($H_2O_2$) were used as stressors to induce cell death to model ALS.

Cell viability after treatment with $H_2O_2$ and TNFα was examined in NCS34 cells, a mouse motor neuron cell line, and in C8-D1A cells, a mouse astrocyte cell line (from the American Type Tissue Culture Collection). The protocol for assessing the activity of any of the compounds disclosed herein in cultured cells is as follows:

Day 1: Cells were plated into 96 well plates at a confluency of 60%. Cells were maintained in growth medium consisting of Dulbecco's Modified Essential Medium (DMEM, LifeTechnologies Inc.) supplemented with 10% fetal bovine serum (Hyclone) and incubated in a tissue culture incubator at 37° C., 95% $O_2$ and 5% $CO_2$.

Day 2: The growth medium was changed to 200 μl/well DMEM without fetal bovine serum. Additional agents, such as varying concentrations of $H_2O_2$ (Sigma Aldrich Inc.), TNFalpha, and a vehicle control or any of the compounds disclosed herein, e.g., NPD1 (Anida Pharma Inc.) were added to the growth medium. The cells were incubated overnight for 24 hours in a tissue culture incubator at 37° C., 95% $O_2$ and 5% $CO_2$ Day 3: After 24 hours, 20 μl of Wst-1 cell viability reagent (Roche Applied Sciences Inc.) was added to each well (1:10 dilution in growth medium). Mix well by gently rocking the plate side-to-side. The cells were incubated at 37° C. for 60 minutes. The absorbance signal was measured by a spectrophotometric multi-well plate reader (Molecular Diagnostics Inc.) with a test wavelength at 450 nm and a reference wavelength greater than 600 nm (for example, 630 nm). A background control (or blank) for the growth medium and WST-1 reagent (without cells) can also be measured. The 630 nm background absorbance values are then subtracted from the 450 nm measurement for a normalized 450 nm absorbance value.

Example 2

NPD1 Treatment Increases Motor Neuron Survival

NPD1, or Compound 1 in Table 1, was analyzed for activity in NCS34 cells, a mouse motor neuron cell line. First, NCS34 cells were treated with increasing concentrations of $H_2O_2$ (1 μM, 10 μM, 50 μM, 100 μM, 400 μM and 800 μM) and 10 ng/ml TNFα for 24 hours to demonstrate that the combination of oxidative stress and inflammation cause motor neuron cell death. Cell viability was determined by Wst-1 cell viability assay, as described in Example 1. Treatment with $H_2O_2$ and 10 ng/ml TNFα caused between 26-37% cell death in the motor neurons (FIG. 1). The average absorbance values and percentage of cell viability are shown in Table 2.

TABLE 2

NCS34 cell viability after $H_2O_2$ + 10 ng/ml TNFα treatment.

| NSC34 cells-24 hrs incub. | Avg Abs450 nm | % Cell Viability |
|---|---|---|
| control (veh.) | 0.7638 | 100 |
| TNFa10 ng/ml | 0.7646 | 100.1047395 |
| TNFa10 ng/ml + H2O2-1 uM | 0.7013 | 91.81722964 |
| TNFa10 ng/ml + H2O2-10 uM | 0.5712 | 74.78397486 |
| TNFa10 ng/ml + H2O2-50 uM | 0.48505 | 63.5048442 |
| TNFa10 ng/ml + H2O2-100 uM | 0.49595 | 64.93191935 |
| TNFa10 ng/ml + H2O2-400 uM | 0.49385 | 64.65697827 |
| TNFa10 ng/ml + H2O2-800 uM | 0.50965 | 66.72558261 |

Figure 2:
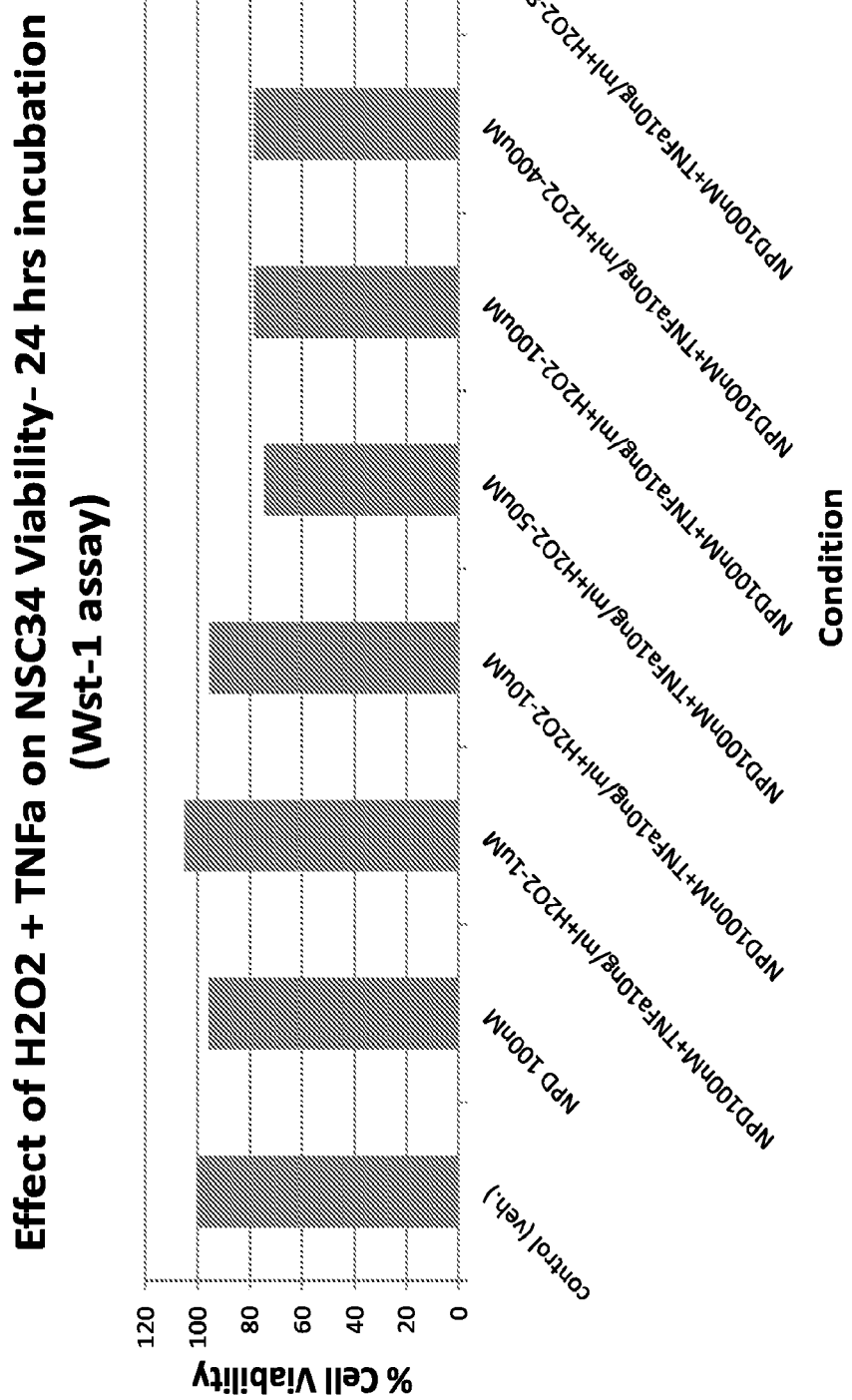
FIG. 2 is a graph depicting the cell viability of NSC34 cells after 24 hours treatment with 100 nM NPD1 and increasing concentrations of $H_2O_2$ (0-800 μM) and 10 ng/ml TNFα.

Treatment of the cells with 100 nM NPD1 increased cell viability after 24 hours of treatment with $H_2O_2$ and 10 ng/ml TNFα (FIG. 2). Average absorbance values and calculated percentage of cell viability are shown in Table 3. The results show that administration of NPD1 to cells treated with 10 μM $H_2O_2$ and 10 ng/ml TNFα resulted in an increase in cell viability from 74.7% (without NPD1) to 95.6% (with NPD1). Similarly, the addition of NPD1 to cells treated with 50-800 μM $H_2O_2$ and 10 ng/ml TNFα also resulted in increases in cell viability.

TABLE 3

NCS34 cell viability after 100 nM NPD1 and $H_2O_2$ + 10 ng/ml TNFα treatment.

| NSC34 cells-24 hrs incub. | Avg Abs 450 nm | % Cell Viability |
|---|---|---|
| control (veh.) | 0.6757 | 100 |
| NPD 100 nM | 0.6462 | 95.63415717 |
| NPD100 nM + TNFa10 ng/ml + H2O2-1 uM | 0.71035 | 105.1280154 |
| NPD100 nM + TNFa10 ng/ml + H2O2-10 uM | 0.64495 | 95.44916383 |
| NPD100 nM + TNFa10 ng/ml + H2O2-50 uM | 0.50315 | 74.46351931 |
| NPD100 nM + TNFa10 ng/ml + H2O2-100 uM | 0.52855 | 78.22258399 |
| NPD100 nM + TNFa10 ng/ml + H2O2-400 uM | 0.5288 | 78.25958266 |
| NPD100 nM + TNFa10 ng/ml + H2O2-800 uM | 0.5501 | 81.41186917 |

Figure 3:
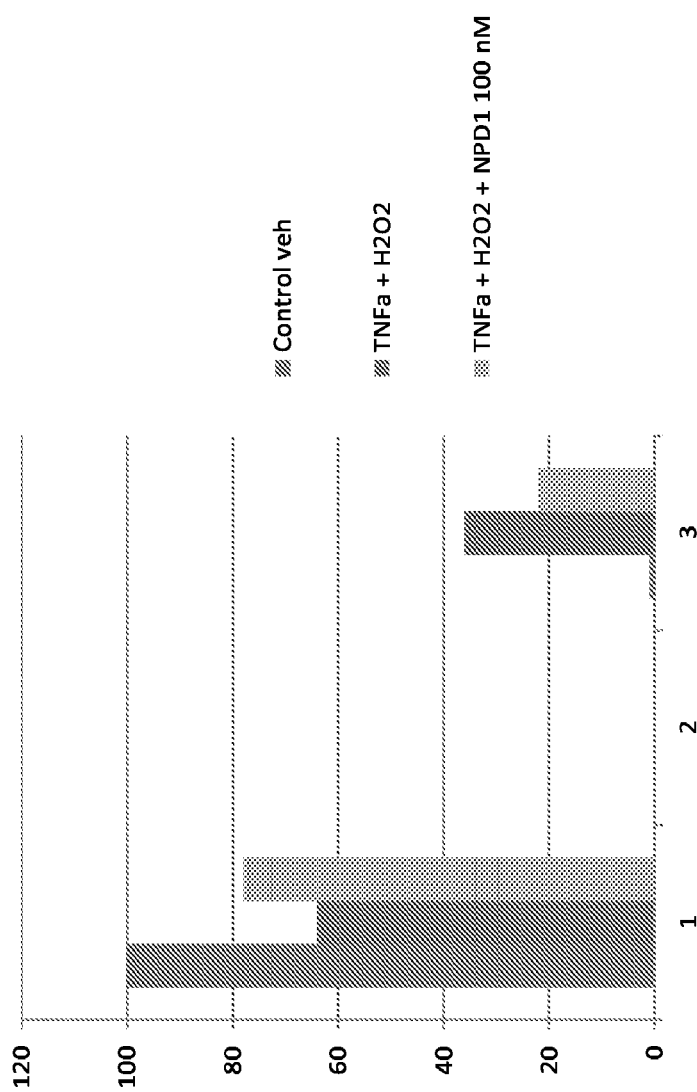
FIG. 3 is a graph summarizing the cell viability and cell apoptosis of NSC34 cells after 24 hours of treatment with either TNFα+$H_2O_2$ alone or with 100 nM NPD1. The set of columns on the left show the percentage of viable cells for each treatment, with vehicle control set to 100%. The set of columns on the right show the percentage of cell apoptosis.

FIG. 3 and Table 4 shows the comparison of the percentage of viable cells and apoptosed cells when NCS34 cells were treated with or without NPD1 in addition to oxidative and inflammation stressors, $H_2O_2$ and TNFα. These results demonstrate that in motor neurons, treatment with NPD1 increases cell survival by 39% over untreated controls.

TABLE 4

Comparison of NCS34 cell viability and apoptosis after NPD1 treatment.

|  | % cell viability | % cells apoptosed |
|---|---|---|
| Control (veh.) | 100 | 1 |
| TNFa + H2O2 | 64 | 36 |
| TNFa + H2O2 + NPD1 100 nM | 78 | 22 |
| Percent saved with NPD1 (14/36) |  | 39% |

Furthermore, the percentages of cell viability and survival may be underestimated in this assay. Greater cell death in the vehicle controls, for example around 40%, would likely have increased the difference in survival after NPD1 treatment. Therefore, NPD1 may confer greater survival advantage to motor neuron cells than demonstrated by these results.

Example 3

NPD1 Treatment Increases Astrocyte Viability

Additionally, it is well recognized in the art that astrocytes play a role in the progression of ALS. Astrocytes are trophically critical for any kind of neuron and interaction between neurons and astrocytes are essential for the health of the former. It is known in the art that trophic factors released from astrocytes could be beneficial in ALS. In addition, it is also well known that astrocytes are the main contributors to glutamate reuptake. Since increased concentration of glutamate is known to cause excitotoxicity resulting in degeneration of motor neurons, improving the function and/or viability of astrocytes should, in addition to any trophic factors release, also contribute to reducing excitotoxicity and would therefore be beneficial to treating ALS patients. In contrast, other studies have suggested that astrocyte activation in ALS contributes to motor neuron death. Since astrocytes clearly play a role in ALS progression, the effects of NPD1 treatment on astrocyte viability were examined to provide information on the etiology of the progression of the disease.

Figure 4:
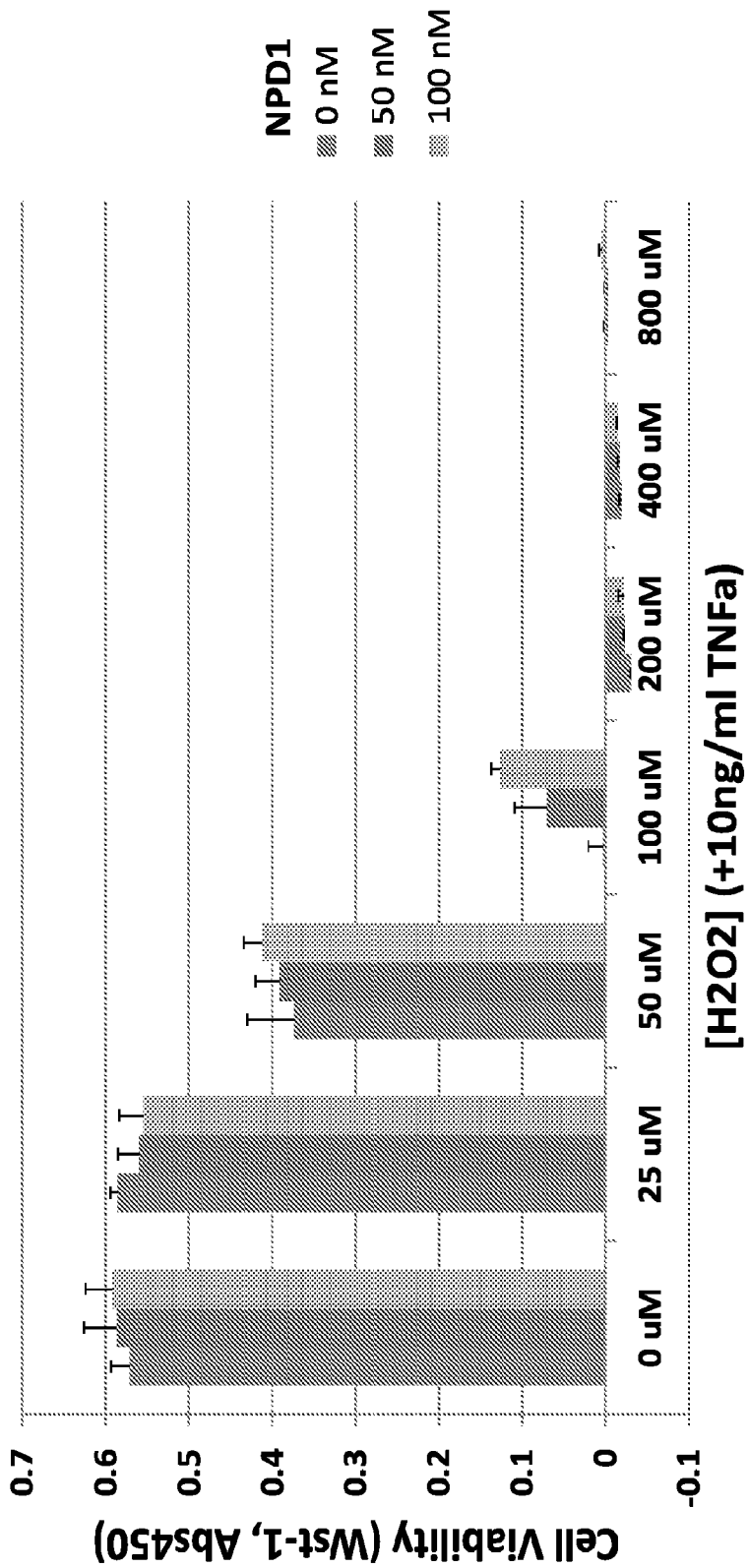
FIG. 4 is a graph depicting the cell viability of C8-D1A cells after 24 hours treatment with varying concentrations of NPD1 (0, 50 and 100 nM) and increasing concentrations of $H_2O_2$ (0-800 μM) and 10 ng/ml TNFα. Cell viability was determined by spectrophotometric reading at 450 nM wavelength.
Figure 5:
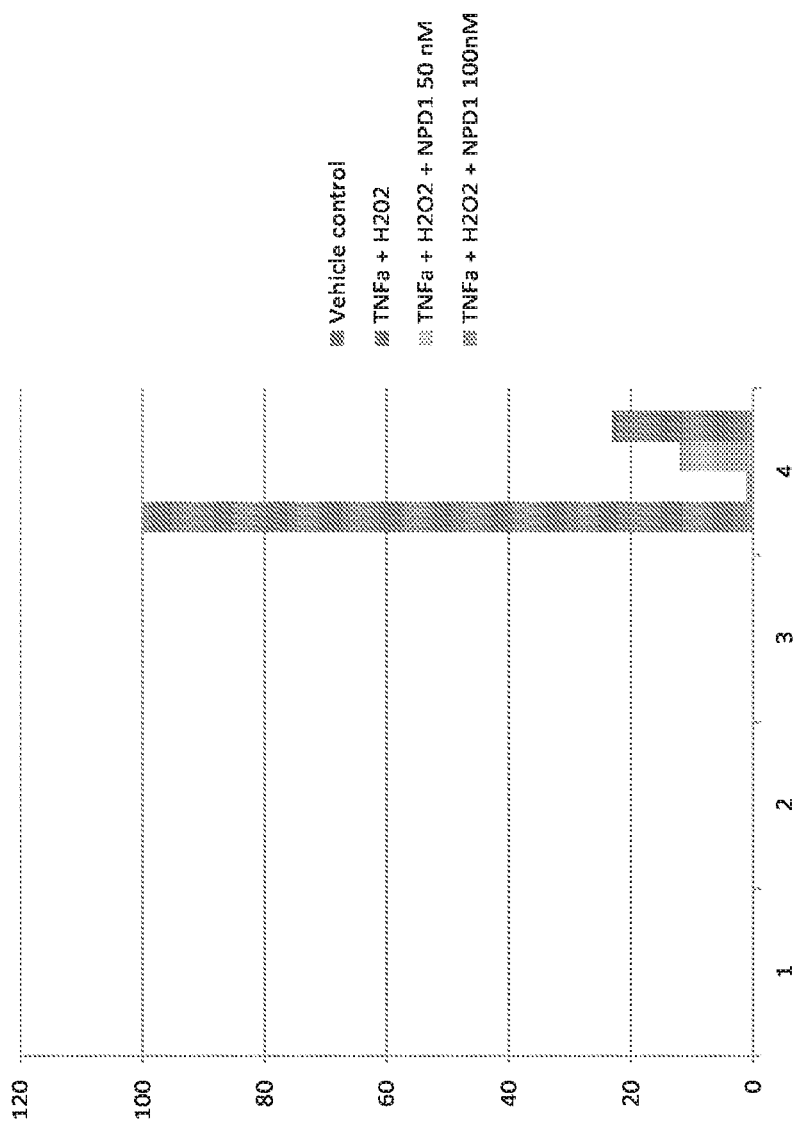
FIG. 5 is a graph summarizing the percentage of surviving C8-D1A cells after 24 hours treatment with varying concentrations of NPD1 (0, 50 and 100 nM) and increasing concentrations of $H_2O_2$ (0-800 μM) and 10 ng/ml TNFα.

NPD1 activity was analyzed in C8-D1A cells, a mouse astrocyte cell line (American Type Tissue Culture Collection). C8-D1A cells were treated with increasing concentrations of $H_2O_2$ (1 μM, 10 μM, 50 μM, 100 μM, 400 μM and 800 μM) and 10 ng/ml TNFα without NPD1, or with 50 nM or 100 nM NPD1 for 24 hours. Cell viability was determined by Wst-1 cell viability assay, as described in Example 1. Each sample was performed in triplicate. Raw and normalized absorbance values are listed in Tables 5 and 6, and a summary of the data is present in Tables 7 and 8. As shown in FIG. 4, treatment with 100 μM $H_2O_2$ and 10 ng/ml TNFα caused significant astrocyte cell death. Cells treated with NPD1 showed increased cell survival and viability in a dose-dependent manner. The beneficial effect of NPD1 treatment on astrocyte cell viability, as calculated as a percentage, is shown in FIG. 5.

TABLE 5

C8-D1A cell viability: raw absorbance data.

| [H2O2] + 10 ng/ml TNFa | 0 nM NPD1 | | | | 50 nM NPD1 | | | | 100 nM NPD1 | | | |
|---|---|---|---|---|---|---|---|---|---|---|---|---|
| | 1 | 2 | 3 | Avg. | 1 | 2 | 3 | Avg. | 1 | 2 | 3 | Avg. |
| 0 uM | 1.0254 | 1.0311 | 0.9902 | 1.015567 | 1.0047 | 1.0764 | 1.0093 | 1.030133 | 1.009 | 1.0312 | 1.071 | 1.037067 |
| 25 uM | 1.0253 | 1.0219 | 1.0398 | 1.029 | 0.9946 | 0.985 | 1.0316 | 1.003733 | 1.0073 | 0.9676 | 1.0219 | 0.998933 |
| 50 uM | 0.7523 | 0.8539 | 0.8459 | 0.817367 | 0.8604 | 0.8427 | 0.8035 | 0.835533 | 0.8776 | 0.8335 | 0.8579 | 0.856333 |

TABLE 5-continued

C8-D1A cell viability: raw absorbance data.

| [H2O2] + 10 ng/ml | 0 nM NPD1 | | | | 50 nM NPD1 | | | | 100 nM NPD1 | | | |
|---|---|---|---|---|---|---|---|---|---|---|---|---|
| TNFa | 1 | 2 | 3 | Avg. | 1 | 2 | 3 | Avg. | 1 | 2 | 3 | Avg. |
| 100 uM | 0.4289 | 0.4646 | 0.4481 | 0.4472 | 0.4731 | 0.5164 | 0.5526 | 0.514033 | 0.5691 | 0.5823 | 0.5639 | 0.571767 |
| 200 uM | 0.4148 | 0.4133 | 0.4128 | 0.413633 | 0.4228 | 0.4206 | 0.4217 | 0.4217 | 0.4166 | 0.4209 | 0.429 | 0.422167 |
| 400 uM | 0.4272 | 0.4226 | 0.4252 | 0.425 | 0.4258 | 0.4267 | 0.4296 | 0.427367 | 0.4289 | 0.4277 | 0.4307 | 0.4291 |
| 800 uM | 0.4453 | 0.4435 | 0.4366 | 0.4418 | 0.4431 | 0.4376 | 0.4439 | 0.441533 | 0.4458 | 0.4484 | 0.4523 | 0.448833 |

TABLE 6

C8-D1A cell viability: absorbance data after subtraction of background signal.

| [H2O2] uM + 10 ng/ml | 0 nM NPD1 | | | | | 50 nM NPD1 | | | | | 100 nM NPD1 | | | | |
|---|---|---|---|---|---|---|---|---|---|---|---|---|---|---|---|
| TNFa | 1 | 2 | 3 | avg | stdev | 1 | 2 | 3 | avg | stdev | 1 | 2 | 3 | avg | stdev |
| 0 | 0.581 | 0.587 | 0.546 | 0.572 | 0.022 | 0.561 | 0.632 | 0.565 | 0.586 | 0.040 | 0.565 | 0.587 | 0.627 | 0.593 | 0.031 |
| 25 | 0.581 | 0.578 | 0.596 | 0.585 | 0.010 | 0.551 | 0.541 | 0.588 | 0.560 | 0.025 | 0.563 | 0.524 | 0.578 | 0.555 | 0.028 |
| 50 | 0.308 | 0.410 | 0.402 | 0.373 | 0.056 | 0.416 | 0.399 | 0.360 | 0.392 | 0.029 | 0.434 | 0.390 | 0.414 | 0.412 | 0.022 |
| 100 | −0.015 | 0.021 | 0.004 | 0.003 | 0.018 | 0.029 | 0.072 | 0.109 | 0.070 | 0.040 | 0.125 | 0.138 | 0.120 | 0.128 | 0.009 |
| 200 | −0.029 | −0.031 | −0.031 | −0.030 | 0.001 | −0.021 | −0.023 | −0.022 | −0.022 | 0.001 | −0.027 | −0.023 | −0.015 | −0.022 | 0.006 |
| 400 | −0.017 | −0.021 | −0.019 | −0.019 | 0.002 | −0.018 | −0.017 | −0.014 | −0.017 | 0.002 | −0.015 | −0.016 | −0.013 | −0.015 | 0.002 |
| 800 | 0.001 | −0.001 | −0.007 | −0.002 | 0.005 | −0.001 | −0.006 | 0.000 | −0.002 | 0.003 | 0.002 | 0.004 | 0.008 | 0.005 | 0.003 |

TABLE 7

C8-D1A cell viability: absorbance data summary.

| | Avg | | | StDev | | |
|---|---|---|---|---|---|---|
| [H2O2] + 10 ng/ml TNFa | 0 nM NPD1 | 50 nM NPD1 | 100 nM NPD1 | 0 nM NPD1 | 50 nM NPD1 | 100 nM NPD1 |
| 0 uM | 0.571567 | 0.586133 | 0.593067 | 0.022152 | 0.040134 | 0.031414 |
| 25 uM | 0.585 | 0.559733 | 0.554933 | 0.009506 | 0.024606 | 0.0281 |
| 50 uM | 0.373367 | 0.391533 | 0.412333 | 0.056491 | 0.029119 | 0.022092 |
| 100 uM | 0.0032 | 0.070033 | 0.127767 | 0.017867 | 0.039803 | 0.009485 |
| 200 uM | −0.03037 | −0.0223 | −0.02183 | 0.001041 | 0.0011 | 0.006296 |
| 400 uM | −0.019 | −0.01663 | −0.0149 | 0.002307 | 0.001986 | 0.00151 |
| 800 uM | −0.0022 | −0.00247 | 0.004833 | 0.004592 | 0.00343 | 0.003272 |

TABLE 8

Comparison of C8-D1A cell viability and apoptosis after NPD1 treatment.

| | % cell viability | % cells apoptosed |
|---|---|---|
| Vehcle control | 100 | 1 |
| TNFa + H2O2 | 1 | 99 |
| TNFa + H2O2 + NPD1 50 nM | 12 | 88 |
| TNFa + H2O2 + NPD1 100 nM | 23 | 77 |

As shown in the Table 8, treatment with NPD1 increased astrocyte viability and reduced astrocyte death. Moreover, increasing dosages of NPD1 increased the survival of astrocytes.

Example 4

In Vivo Models of ALS

In vivo models of ALS are known in the art and may be useful for demonstrating the efficacy of treatment of any of the compounds of the present invention on the delay or alleviation of ALS symptoms and progression. For example, genetic models in *C. elegans, D. melanogaster, D. rerio* and rat utilizing RNAi or mutations in genes known to be involved in the progression of ALS have been developed. The genes known to be involved in or model ALS progression include, for example, SOD1, TDP-43, ATAXN3 (*D. melanogaster*), FUS/TLS, and ALS2. Particularly preferred in vivo models include mouse models of ALS, such as mice containing mutations in SOD1, TARDBP (TDP-43) or ALS2 (alsin). SOD1 mutations may include G37R, G85R, G86R, D90A, G93A, H46R/H48Q, H46R/H48Q/H63G/H120G, L126Z and G127X. TARDBP (TDP-43) mutations may include A315T, G348C, M337V or a combination thereof. ALS2 knockout mice or loss of function mutations may be preferred. Examples of such mouse models include: B6SJL-Tg (SOD1-G93A)1Gur/J, B6SJL-Tg(SOD1)2Gur/J, B6.Cg-Tg (SOD1-G93A)1Gur/J, B6.Cg-Tg (Prnp-TARDBP-A315T)95Balo/J, and STOCK Tg(Pmp-TARDBP-A315T)23J1e1/J.

Assays to determine toxicity of compounds of the present invention, such as NPD1, are well-established in the art and can be performed in mice. For example, NPD1 compositions at varying dosages dosage from about 0.01 to about 50 mg per kg per day can be administered to mice via intranasal, intracerebroventricular (ICV), and intrathecal administration. Dosages can be administered once, twice, or more than twice over a predetermined time period. For example, NPD1 and a control can be administered every 3 to 4 days, every week, or once every two weeks, for up to a year. Mice are monitored for the predetermined time period for symptoms of toxicity or death.

Administration of any of the compounds of the present invention, such as NPD1, in any of the in vivo animal models described herein can also be performed to assess ability to delay or alleviate symptoms of ALS. For example, NPD1 can be administered via intranasal, intracerebroventricular (ICV), and intrathecal administration. Other therapeutic agents known in the art can also be administered simultaneously, prior to or after NPD1 administration. NPD1 can be administered at dosages based on the results from the toxicity assays described above. For example, the dosage can be 0.1-20 mg/kg, more preferably 1-10 mg/kg, and administered at regular intervals over a predetermined time period. Control animals and NPD1-treated animals are monitored for ALS symptoms, such as twitching, cramping, stiffness of muscles, muscle atrophy, paralysis, difficulty eating or breathing and death. Further analysis of motor neuron or astrocyte survival after treatment with NPD1 can also be performed in the animals using methods known in the art.

What is claimed is:

1. A method for reducing oxidative stress associated with amyotrophic lateral sclerosis (ALS) comprising administering to a subject in need thereof a therapeutically effective amount of a compound of Formula I:

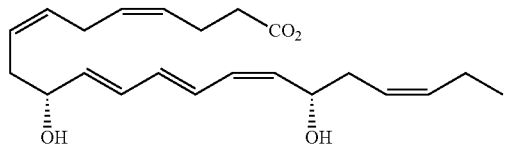

or a pharmaceutically acceptable salt, ester, solvate, hydrate or prodrug thereof, wherein reducing oxidative stress associated with ALS comprises one or more of (a) reducing cell death; (b) reducing neurodegeneration; or (c) increasing cell survival of a cell from the subject suffering from ALS, wherein said cell is a motor neuron and said method increases motor neuron survival by at least 39%.

2. The method of claim 1 wherein said compound of Formula I or a pharmaceutically acceptable salt, ester, hydrate, solvate, prodrug, metabolite, analog or derivative thereof is in combination with a pharmaceutically acceptable excipient.

3. The method of claim 1 wherein reducing oxidative stress associated with ALS alleviates at least one symptom of ALS.

4. The method of claim 3, wherein the symptom of ALS is selected from: twitching, cramping or stiffness of muscles; muscle weakness affecting an arm of a leg; muscle atrophy; slurred and nasal speech; shortness of breath; and difficulty chewing, swallowing or breathing.

5. The method of claim 1, wherein reducing oxidative stress associated with ALS prolongs or increases the survival of the subject suffering from ALS.

6. The method of claim 1, wherein the compound is sodium (4Z,7Z,10R,11E,13E,15Z,17S,19Z)-10,17-dihydroxydocosa-4,7,11,13,15,19-hexaenoate or (4Z,7Z,10R,11E,13E, 15Z,17S,19Z)-10,17-dihydroxydocosa-4,7,11,13,15,19-hexaenoic acid.

7. The method of claim 1, further comprising administering at least one second active therapeutic agent.

8. The method of claim 7, wherein the second active therapeutic agent is selected from riluzole, talampanel (8-methyl-7H-1,3-dioxolo(2,3)benzodiazepine), Tamoxifen, TCH346, Vitamin E, Celecoxib, Creatine, Copaxone, NP001, ozanezumab, Gilenya, SOD1Rx, MC1-186 and combinations thereof.

9. The method of claim 1, wherein the compound is administered at a dosage from about 0.01 to about 50 mg per kg per day.

10. The method of any of the preceding claims, wherein the route of administration is selected from intranasal, intracerebroventricular (ICV) and intrathecal administration.

11. A method for reducing oxidative stress associated with amyotrophic lateral sclerosis (ALS) comprising administering to a subject in need thereof a therapeutically effective amount of a compound of Formula I:

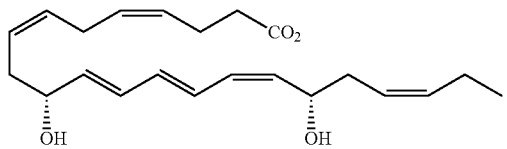

or a pharmaceutically acceptable salt, ester, solvate, hydrate or prodrug thereof, wherein reducing oxidative stress associated with ALS comprises one or more of (a) reducing cell death; (b) reducing neurodegeneration; or (c) increasing cell survival of a cell from the subject suffering from ALS, wherein said cell is an astrocyte and said method increases astrocyte survival by at least 22%.

12. The method of claim 11 wherein said compound of Formula I or a pharmaceutically acceptable salt, ester, hydrate, solvate, prodrug, metabolite, analog or derivative thereof is in combination with a pharmaceutically acceptable excipient.

13. The method of claim 11 wherein reducing oxidative stress associated with ALS alleviates at least one symptom of ALS.

14. The method of claim 13, wherein the symptom of ALS is selected from: twitching, cramping or stiffness of muscles; muscle weakness affecting an arm of a leg; muscle atrophy; slurred and nasal speech; shortness of breath; and difficulty chewing, swallowing or breathing.

15. The method of claim 11, wherein reducing oxidative stress associated with ALS prolongs or increases the survival of the subject suffering from ALS.

16. The method of claim 11, wherein the compound is sodium (4Z,7Z,10R,11E,13E,15Z,17S,19Z)-10,17-dihydroxydocosa-4,7,11,13,15,19-hexaenoate or (4Z,7Z,10R, 11E,13E,15Z,17S,19Z)-10,17-dihydroxydocosa-4,7,11,13, 15,19-hexaenoic acid.

17. The method of claim 11, further comprising administering at least one second active therapeutic agent.

18. The method of claim 17, wherein the second active therapeutic agent is selected from riluzole, talampanel (8-methyl-7H-1,3-dioxolo(2,3)benzodiazepine), Tamoxifen, TCH346, Vitamin E, Celecoxib, Creatine, Copaxone, NP001, ozanezumab, Gilenya, SOD1Rx, MC1-186 and combinations thereof.

19. The method of claim 11, wherein the compound is administered at a dosage from about 0.01 to about 50 mg per kg per day.

20. The method of claim 11, wherein the route of administration is selected from intranasal, intracerebroventricular (ICV) and intrathecal administration.

* * * * *